United States Patent [19]

Klokkers-Bethke et al.

[11] Patent Number: 5,472,710
[45] Date of Patent: Dec. 5, 1995

[54] PHARMACEUTICAL PREPARATION TO BE ADMINISTERED ORALLY WITH CONTROLLED RELEASE OF ACTIVE SUBSTANCE AND METHOD FOR ITS MANUFACTURE

[75] Inventors: Karin Klokkers-Bethke, Monheim/Rhld.; Wilfried Fischer, Burscheid, both of Germany

[73] Assignee: Schwarz Pharma AG, Monhiem, Germany

[21] Appl. No.: 235,188

[22] Filed: Apr. 29, 1994

Related U.S. Application Data

[63] Continuation of Ser. No. 956,456, Oct. 2, 1992, abandoned, which is a continuation-in-part of Ser. No. 337,636, Apr. 13, 1989, abandoned.

[30] Foreign Application Priority Data

Apr. 16, 1988 [DE] Germany .......................... 38 12 799.7

[51] Int. Cl.⁶ .............................. A61K 9/22; A61K 9/24; A61K 9/52
[52] U.S. Cl. .......................... 424/468; 424/469; 424/470; 424/471; 424/472; 424/473; 424/474; 424/475; 424/479; 424/480; 424/481; 424/482; 424/457
[58] Field of Search .................................. 424/468–482, 424/457–463

[56] References Cited

U.S. PATENT DOCUMENTS

| | | | |
|---|---|---|---|
| 4,627,851 | 12/1986 | Wong et al. | 604/892 |
| 4,828,840 | 5/1989 | Sakamoto et al. | 424/474 |
| 4,863,742 | 9/1989 | Panoz et al. | 424/471 X |

FOREIGN PATENT DOCUMENTS

| | | |
|---|---|---|
| 0040590 | of 0000 | European Pat. Off. . |
| 0202051 | of 0000 | European Pat. Off. . |
| 0225189 | of 0000 | European Pat. Off. . |
| WO8700044 | of 0000 | WIPO . |

OTHER PUBLICATIONS

M. Saferan et al—"A New Approach to the Oral Administration of Insulin and Other Peptide Drugs"—Science, vol. 233, 5 Sep. 1986, pp. 1081–1084.

C. Bogentoft et al.—"Delivery of Drugs to the Colon by Means of a New Microencapsulated Oral Dosage Form"—Short Communication, Acta. Pharm. Suec. 20.311–314 (1983).

Arzneimittelkommission der Deutschen Apotheker—Pharmazeutische Zeitung, 128, Jahrgang Nr. 34–25 Aug. 1983, pp. 1845–1846.

H. Bechgaard et al—"Gastrointestinal Transit Time of Single–Unit Tablets"—J. Pharm. Pharmacol. 1981, 33: 791–792 Communicated Apr. 8, 1981.

Michael G. Velchik, M.D., James H. Thrall, M.D.—"Gastroenterology III: Lower GI"—The Journal of Nuclear Medicine, vol. 25, No. 5, pp. 59–60, Jun. 1984.

S. S. Davis et al—"Transit of Pharmaceutical Dosage Forms Through the Small Intestine"—Department of Pharmacy, University of Nottingham, Gut. 1986, 27, 886–892.

S. S. Davis—"The Design and Evaluation of Controlled

(List continued on next page.)

Primary Examiner—Gollamudi S. Kishore
Attorney, Agent, or Firm—Marshall, O'Toole, Gerstein, Murray & Borun

[57] ABSTRACT

Pharmaceutical preparation to be administered orally with controlled release of active substance and method for its manufacture. Pharmaceutical preparation to be administered orally with controlled release of active substance, containing a nucleus which itself consists at least of one pharmacologically active substance, or a nucleus of physiologically safe material which is enveloped by an active substance layer, containing at least one pharmacologically active substance, if needed, a first membrane, then an acid layer consisting at least of a physiologically safe acid and then a compound membrane consisting of a pH sensitive polymer and an insoluble polymer, as well as methods for its manufacture. The pharmaceutical preparation is applicable to all claimed types of medicine and to the therapy of illnesses.

19 Claims, 4 Drawing Sheets

OTHER PUBLICATIONS

Release Systems for the Gastrointestinal Tract"—Department of Pharmacy, University of Nottingham, pp. 27–38, 1985.

S. S. Davis et al—"The Effect of Food on the Gastrointestinal Transit of Pellets and an Osmotic Device (OSMET)"—International Journal of Pharmaceutics, 21 (1984) 331–340.

Goetz "Vorrichtung zur Verabreichung Eines Wirkstoffes an Das Kolon"—pp. 2–21—Alza Corp.

H. Schroder et al—"Absorption, Metabolism, and Excretion of Salicylazosulfapyridine in Man"—Department of Zoophysiology, University of Uppsala, Clinical Pharmacology and Therapeutics, vol. 13, No. 4, pp. 539–551, 1972.

R. Khosla et al—"The Effect of Polycarbophil on the Gastric Emptying of Pellets"—J. Pharm. Pharmacol. 1987, 39: 47–49, Communicated Jul. 14, 1986.

J. Urquhart, M.D. et al—"Delivery Systems & Pharmocodynamics in New Drug Research & Development"—Presented at Biotech 1985.

D. Ganderton—"Current Innovatins in Drug Delivery" pp. 2–7, 1987.

A. L. Golub, Ph.D. et al—"Physiologic Considerations in Drug Absorption from the Gastrointestinal Tract"—Key Pharmaceuticals, Inc., J. Allergy Clin. Immunol., Oct., 1986, pp. 689–694.

M. Saferan et al—"A New Approach to the Oral Administration of Insulin and Other Peptide Drugs"—Science, vol., 233, 5 Sep. 1986, pp. 1081–1084.

FIG. 1

FIG. 2
DILTIAZEM PLASMA LEVEL – MR. A.F.

FIG. 3
DILTIAZEM PLASMA LEVEL – MR. W.G.

FIG. 4
DILTIAZEM PLASMA LEVEL – MR. D.J.

---- FORMULA EX. 1
—— FORMULA EX. 2

FIG. 5
DILTIAZEM PLASMA LEVEL – MR. K.A.

---- FORMULA EX. 1
—— FORMULA EX. 2

FIG. 6
DILTIAZEM PLASMA LEVEL – MR. W.E.

FIG. 7
DILTIAZEM PLASMA LEVEL – MR. O.D.

PHARMACEUTICAL PREPARATION TO BE ADMINISTERED ORALLY WITH CONTROLLED RELEASE OF ACTIVE SUBSTANCE AND METHOD FOR ITS MANUFACTURE

This is a continuation of U.S. application Ser. No. 07/956,456, filed Oct. 2, 1992, now abandoned; in turn a C-I-P of Ser. No. 07/337,636 filed Apr. 13, 1989, now abandoned.

This invention deals with a pharmaceutical preparation to be administered orally with controlled release of an active substance and a method for its manufacture as it is individually characterized in the patent claims.

It has been known to use sustained-release drug formulations in order to reduce the frequency of administration and to minimize side effects by preventing plasma level peaks. In this way, patient compliance is increased. Ideally, one daily dose of the prescribed medicine is desired.

The attainability of this goal depends:

On the one hand, on the characteristics of the pharmaceutical as, for example, biological half-life; absorption characteristic and tolerance development;

On the other hand, on the characteristics of the employed sustained-release type medicine as, for example, the release profile of the active substance and its retention in the absorbing gastrointestinal portions.

Standard sustained-release types of medicine release the active substance in less than eight hours, "long sustained action" types of medicine have a release time of more than eight hours. These conventional sustained-release types have in common a release rate with an approximately constant time factor.

Pharmaceuticals which are expected to lead to the development of tolerance formation after chronic use (for example, nitrates, corticosteroids), or their activity or an undesirable side effect of their administration varies with the time of the day (for example, glucocorticoids), should be used at intervals with active substance, and quasi "active substance-free", blood levels, that are at least below the tolerance or toxicity threshold (J. Urquhart, Delivery Systems & Pharmacodynamics in New Drug Research & Development, BIOTECH 1985 USA, Online Publications, Pinner, UK 1985, p. 321–331). They are not suitable for single or twice daily doses in long sustaining formulations which uniformly release the active substance. In this case, there is a danger that an impairment of effectiveness, or side effects, will occur during constant plasma levels through physiological counteraction. Medicinal types which, after a single dose, result in several plasma level peaks and troughs, for example, would lower or even prevent tolerance formation. In addition, intake frequency would be lowered, and compliance would be increased.

Such pulsating plasma levels cannot be obtained with conventional sustained-release types of drug formulations which give a constant rate of release over a period of time. When sustained release types are properly designed in accordance with the state of the art, a more or less constant plasma level plateau is obtained, and it is quickly attained by administering an initial dose in cases where this is necessary. After a certain time, which is determined by the transit time of the sustained-release type through the absorbing gastrointestinal portions in combination with the selected release time, the plasma levels drop until the next time of administration. Thus, a renewed surge of active substance following a single administration is not possible (D. Ganderton, Drug Design and Delivery, 2, 1–7 (1987). But this is just what is necessary for the formation of a fluctuating plasma level.

Pharmaceuticals which are not subject to a decline in constant plasma level effectiveness, as a rule, cannot achieve uniform plasma level patterns even over a time of 24 hours through the administration of a long-term sustained-release, e.g., a continuously releasing sustained-release medicinal formulation. On the average, 6 to 8 hours after the application, the sustained-release medicinal types, at least on an empty stomach, and independently, whether they were given as a single or a multiple dose, enter the lower small intestine portions like the distal ileum or the colon. For the overwhelming number of pharmaceuticals, the absorption rate is reduced with respect to these portions of the small intestine area. If a sustained-release formulation releases the active substance at a constant rate, this unavoidably leads to a lowering of the plasma level. Besides the specific absorption characteristic of the pharmaceutical, the reduction of the water content in the lower small intestine and the colon, altered solution ratios and diffusion ratios, and the increasing viscosity of the intestine content lead to a general, non-specific absorption deterioration of the active substances from various drug formulations. Only a few examples are known as, for example, Theophyllin, Metoprolol (A. L. Golub et al., J. Allergy, Clin. Immunol, 78, 689–694 (1986); G. Ragnarson et al. Development of a New, Controlled Release Metoprolol Product, 6th Pharmaceutical Technology Conference, Canterbury, England, 1987, Vol. I, p. 65–81) where uniform plasma levels were obtained over a 24 hour period with long sustained-release medicinal formulations.

Long sustained-release medicinal formulations lead to an active substance release over such a period of time that a portion of the dose reaches the intestine portions with less efficient absorption. This partial dose cannot be used by the organism to the same extent as that part of the dose released in the remaining intestinal portions. Bio-availability losses are the consequence. Proportionally less medicine is absorbed than in the upper intestine portions. It is recommended, for that reason (R. Khosla and S. S. Davis, J. Pharm. Pharmacol, 39, 47–49 (1987); D. Ganderton, Drug Design and Delivery, 2, 1–7 (1987), that a sustained-release time of 8 to 12 hours not be passed, in order not to have to incur too high a bio-availability loss. This can happen when the release time in vivo is so long that the sustained-release type is excreted together with the portion of the dose which has not been absorbed.

It would be an advantage to have medicinal types which supply medicines to the organism by taking into consideration the corresponding absorption rates in such a manner that, upon administration of a single dose per day over a desired period, constant plasma levels result. This can mean that the medicinal formulation must release the medicinal substance at a higher rate in the colon, for example, than in the other intestinal portions.

Controlled release drug formulations which are to release the entire dose or a partial dose of the active substance in the large intestine, must be designed so that they, with the aid of an active substance release-free period of time (lag phase) or by a signal provided by the large intestine milieu, start to release the active substance. In the first case, the release-free interval must be so calculated that, after the expected transit time between intake and arrival at the colon, the active substance is available there.

Possible signals can be provided by colon-specific enzymes from the large intestine. For example, it has been known that, preferably in the colon area, substances containing azo-groups are bacterially reduced (H. Schroeder and D. E. S. Campbell, Clin. Pharmacol. Ther., 13, 539 (1972).

Depending on the pharmaceutical used, its absorption rate from the colon can be so low that use of a sustained-release active substance which is released in the colon area is useless. Medicinal formulations which are slowly absorbed by the lower intestinal portions have to be quickly released there. Due to the thus achieved increase in concentration of the active substance in the respective absorption area, with assumed increasing passive diffusion according to the Fick Law, the active substance transported through the large intestine mucous membrane can be increased.

As is known from the literature, previous attempts have been made to target the colon as the organ in which to release the active substance present in sustained-release medicinal formulations. Thus, DOS 3538038 A1, DOS 3538040 A1 and the U.S. Pat. No. 4,627,851 describe osmotic systems which are not intended to release the active substance contained in them prior to reaching the colon. The release rates, however, are constant and besides are so small (between 10 and about 80% in 26 to 28 hours) that there is a danger that excretion of the formulation will occur while it still contains the medicine. In practice, the result is a possible loss of an unpredictable portion of the drug dose and, consequently, an uncontrollable decrease in bio-availability.

This behavior of the thus provided osmotic systems, which cannot be modified, contradicts the basic idea of a medicinal formulation having controlled release of the active substance. The transit time of such a single-dose medicinal formulation to the colon is unpredictable in an individual case when the administration takes place after, or together with, a meal (S. S. Davis et al. Int. J. Pharmaceutics, 21, 331–340 (1984). It can take over 10 hours in an extreme case and is subject to very strong variation between individuals. (H. Bechgaard and K. Ladefoged, J. Pharm. Pharmacol., 33, 791–792 (1981). The time after which the dose of active substance is available for absorption is consequently uncontrollable. This can lead to a loss of effectiveness which is unacceptable. Consequently, medicinal effectiveness is not assured.

Osmotic systems, such as those of the above-named patents, are known to strongly damage the mucous membranes in individual cases (outburn effect) (Pharm. Ztg,. 128, 1845 (1983), which can lead to ruptures through the stomach or small intestine wall respectively. This is due to the very small outlet openings in the pharmaceutical product and consequently to the high concentration of active substance at the outlet locations.

In addition, manufacture of the osmotic systems is expensive and prolonged. Their manufacture requires use of complicated technologies (for example: laser technology) in order to create the required precise holes in the osmotically active membranes.

C. Bogentoft et al., Acta Pharm. Suec. 20, 311–314 (1983) and EPA 0040 590 describe medicinal formulations based on multiple dose active substance carriers, which are to release the active substances for the local treatment of intestinal inflammations (salicylazo-sulfapyridine, 5-aminosalicylic acid, cholestyramine) in the colon. According to the patent application, active substance nuclei are covered with a layer of a carboxyl-containing anionic polyacrylate and thereafter with a layer of a polyacrylate containing quarternary ammonium groups. Release of the active substance from this system is highly pH dependent. The water insoluble outer membrane serves to delay water diffusion into the granule and active substance diffusion out of the granule. This becomes obvious from the thickness of this layer, which can amount to 15–90% of the entire covering. This medicinal type evidently represents a diffusion-controlled system (water-insoluble outer layer), where the membrane thickness decreases depending on the pH value. In an acidic medium a diffusion membrane (the inner layer, and the outer layer, cannot be dissolved by the gastric juice) of maximum thickness controls the diffusion; in a neutral or an alkaline medium, after dissolution of the inner layer only the remaining outer layer controls the diffusion. In conformity with the total layer thickness, the resulting lag phase is pH dependent.

This type does not do justice to the pH variations of the gastrointestinal tract between individuals. The above-mentioned requirement for quick release of an active substance into the colon, in case of need, is thus not met.

M. Saffran et al., Science, 233, 1081–1084 (1986) describe a coating material for tablets which is split by reducing bacteria in the colon. The previously insoluble polymer dissolves in the colon and exposes the tablet nuclei. The authors suggest this system for oral insulin therapy. The releasing speed from this medicinal type depends directly on bacteria colonization in the colon and consequently is subject to strong individual variations and variations between different individuals, which particularly endanger the therapeutic success of insulin.

EP 227814-A claims to increase the release rate at that point where the absorption capacity of the organism is reduced. The medicinal type is a matrix tablet. The matrix releases bimodally in vitro upon use of bimodally distributed hydroxypropylmethyl cellulose. A correlation in vivo is missing where, particularly with respect to hydrogel formers, the swelling and thus the active substance release strongly depends on the surrounding medium, its ion strength, ion type and nourishment, type of nourishment as well as mechanical stress. The monolithic medicinal type of the matrix tablet is less predictable than multiple dose types with respect to the transit time in the gastrointestinal tract. Whether an increase in the release rate in vitro also takes place in vivo at the right time and at the right location cannot be reliably predicted. As seen from the examples of the embodiment, time intervals free of active substance release cannot be created.

EP 202051-A also claims to provide a once-daily dose via a combination of various releasing pellet types filling a capsule. It is conceived with normal sustained-release pellets which also do not guarantee intervals which are free of active substance release.

FR 2565107-A describes granules built up of concentric layers of active substances and auxiliary substances with an asserted active substance release at the desired active location, with substantiation for this missing, and where with this pellet structure that does not contain any specific element which controls release of the active substance, the reason for such behavior is also not explained. Phases without active substance release cannot be achieved by this type.

DE 3424648-A and DE 3329265-A describe normal continuously releasing matrix medicinal types, and claim they are suitable for a once-daily dose, without taking into consideration the different ratios of absorption at various locations in the gastrointestinal tract. As is becomes obvious from the examples of the embodiment, time intervals free of active substance release cannot be created.

DE 3331262 and EP 0225189 claim to release medicine at defined locations in the digestive tract solely by pH control. This exclusive pH control is an unsuitable release signal based on the large interindividual fluctuations and variations between different individuals and, above all, because of missing pH jumps in the gastrointestinal tract.

It is an object of this invention to provide a medicinal type which eliminates the above-described dangers and disadvantages and, to a large extent independently of, among others, variations between individuals of the pH value and the bacterial flora in the gastrointestinal tract, releases the incorporated active substance at a predetermined location or a predetermined time and ensures an optimum bioavailability. The medicinal formulation is to start release of the active substance at a predetermined time and to provide if necessary, in combination with immediately releasing dose portions, fluctuating plasma levels for a therapy adjusted to particular needs.

The lag phase prior to the release of a defined dose is, in particular, to be so measured that the upper colon area (colon ascendens) can be safely reached and the active substance be supplied there at a predetermined rate to the colon. The release rate is to be so calculated that, adjusted to the respective individual therapy requirement, high and long lasting plasma levels or concentrations in the intestinal lumen can be achieved with locally active substances. Thus, in combination with a dose portion, corresponding to the customary sustained-release, the once-daily dose of suitable medicinal formulations is made possible.

This object is met according to this invention in that a nucleus is surrounded by an active substance-containing layer which contains at least one pharmacologically active substance, then a first membrane layer, then an acid layer which comprises at least one physiologically absolutely safe acid, and then a compound membrane which may also be called a composite membrane.

According to one embodiment, the nucleus itself comprises at least one pharmacologically active substance.

In a further development, the active substance layer can contain at least one suitable pharmacologically active substance, the first membrane can be soluble independently or dependently of the pH; the acid layer can comprise a member of the group consisting of sodium dihydrogen phosphate, citric acid, tartaric acid, succinic acid and fumaric acid (without being restricted to these) and/or mixtures thereof; and the compound membrane can comprise a pH sensitive polymer inner layer and an insoluble polymer outer layer. According to another further development of this invention the first membrane can be a cellulose acetate phthalate. The first membrane (optional) is not permeable for the active substance. The first membrane is dissolved when the acid layer is exhausted in the gastrointestinal fluids. Then release of the active substance starts through the insoluble polymer part or outer layer of the compound membrane. Thus, the acid layer determines the duration of the time interval without any active substance release after intake of the pharmaceutical preparation. The pH sensitive polymer inner layer of the compound membrane also is protected from dissolution by the acid layer, which provides an acidic pH within the product even if the gastrointestinal fluids have an alkaline pH value. The insoluble polymer outer layer of the compound membrane is permeable for the acid, the active substance and water. It protects the pH sensitive polymer inner layer of the compound membrane from dissolution from the outside when the gastrointestinal fluids become alkaline. After exhaustion of the acid layer it can be used to adjust a certain active substance release rate by diffusion.

It is advantageous, in the compound or composite membrane, for the pH sensitive polymer inner layer to comprise copolymers of methacrylic acid and methacrylic acid methyl ester, carboxymethylethyl cellulose, cellulose acetate phthalate, cellulose acetylphthalate, cellulose diacetylphthalate, cellulose triacetylphtalate, hydroxypropylmethylcellulose phthalate, sodium cellulose acetatephthalate, cellulose esterphthalate, cellulose ether phthalate, cellulose esteretherphthalate, hydroxypropyl cellulose phthalate, methyl cellulose phthalate, keratin, keratin-sandarac-tolubalsam, salol, salol-β-naphtylbenzoate and acetotannin or salol with perubalsam, without being restricted thereto, or mixtures of these polymers among one another and/or soluble or insoluble polymers. Furthermore, it is desirable that the insoluble polymer outer layer be ethylcellulose or be cellulose ether, which can contain a copolymersate of acrylic- and methacrylic acid esters with quarternary ammonium groups or polyvinylacetate, without being restricted to these, and/or mixtures thereof and/or portions of soluble polymers.

It is particularly advantageous that the compound membrane contain pore-forming substances. Some useful pore-forming substances are lactose, talcum, titanium and other pigments.

Furthermore, it is of advantage that the polymer portion of the insoluble polymer outer layer of the compound membrane amount to 1 to 30 percent per weight of the compound membrane.

According to a particularly advantageous further development of this invention the active substance layer can contain, in addition to at least one pharmacologically active substance, at least one absorption promoter and/or at least one solubilizer.

In addition, the active substance layer and the acid layer can be combined into one layer, that the layer contain at least one pharmacologically active substance, and that at least a physiologically safe acid be present in the active substance-acid mixture.

According to another embodiment of this invention the first membrane can be excluded.

Furthermore the medicinal formulation can be in the form of a tablet, a pellet, a capsule, a granule, a pill, or a dragee.

Furthermore the pharmaceutical preparation according to this invention can be manufactured by coating a physiologically safe nucleus with at least one pharmacologically active substance on which, if needed, a first membrane layer is applied, and on the latter an acid layer is applied, onto which the compound membrane is deposited.

According to an advantageous process development the various layers are applied by agglomeration, spraying on in a fluidized bed vessel, applied by hand, by a powder dosing device, by pressing, punching, gluing such as in a coating pan, extruding, immersing and/or rolling onto the nucleus containing the active substance.

Finally, the pharmaceutical preparations according to this invention are useful in the therapy of illnesses.

We now provide the following detailed description of the invention.

It has been found through many tests that the time of passage of a pharmaceutical through the small intestine is almost constant, and is within three to four hours; (S. S. Davis, J. Contr. Release, 2, 27–38 (1985) and J. G. Davis et al., Gut, 27, 88614 892 (1986)). It is important to use this time period for a release-free interval. The evacuation of the stomach and the pH change connected therewith was to serve as the starting signal for the mentioned time period. By incorporating an internal buffer system into a medicinal formulation coated with a compound membrane, the detachment of the pH sensitive membrane is temporarily delayed and thus a lag phase is created. A liquid served as test medium. It had a pH value above that which was necessary for the dissolution, of the pH sensitive polymer inner layer of the compound membrane.

Surprisingly, a compound membrane from compositions according to this invention is able to provide the desired time control in cooperation with a physiologically safe acid included in the medicinal formulation. Furthermore, it was surprising that the insoluble polymer outer layer of the compound membrane can be applied in such a thin layer so that it does not act as a membrane controlling release of the active substance.

Solid dispensing types are possible as medicinal preparations like tablets, pellets, capsules, granules, pills, and dragees. Particularly, pellets and granules are suitable as active substance carriers. These types are subject to a reproducible kinetic movement in the gastrointestinal tract. The transit time after leaving the stomach to reach the colon is easily predictable and independent of nourishment intake (S. S. Davis et al., Int. J. Pharmaceutics, 21, 331–340 (1984). Typically it amounts to three to four hours (J. G. Hardy, J. Nucl. Med., 25, 59 (1984).

Controlled release drug formulations comprising compositions according to this invention characterize themselves in that, after leaving the stomach, arbitrary long time intervals during which there is little active substance release can be achieved. After this time period the active substance can be released at a rate which is variably adjustable.

Figure 1:
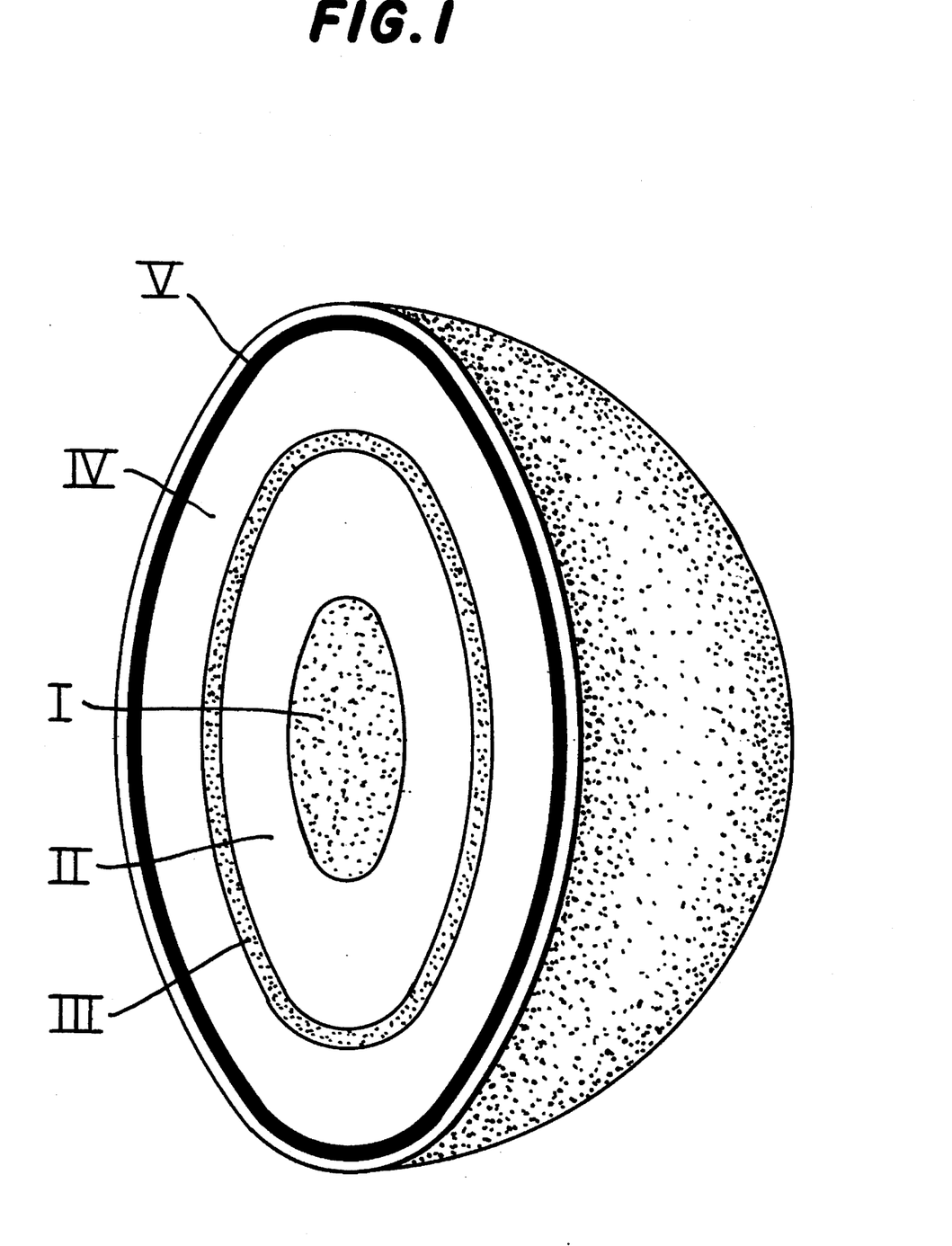
FIG. 1 illustrates one embodiment of a medicinal preparation of the present invention.
Figure 2:
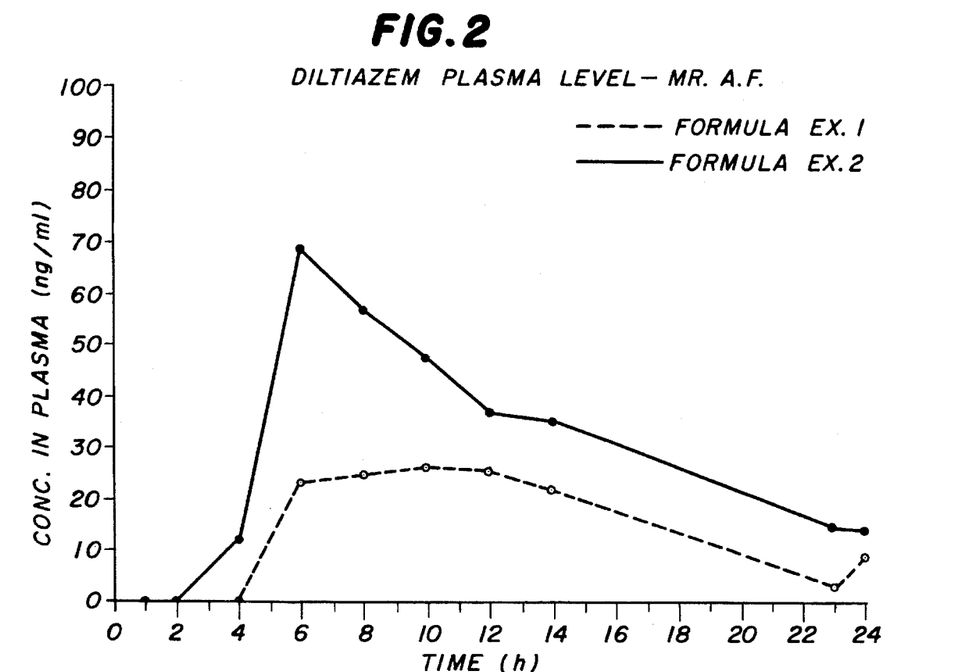
FIGS. 2–7 are plots of diltiazem concentration in plasma (ng/ml) vs. time (hours) in six human volunteers administered the compositions of Examples 1 and 2.
Figure 3:
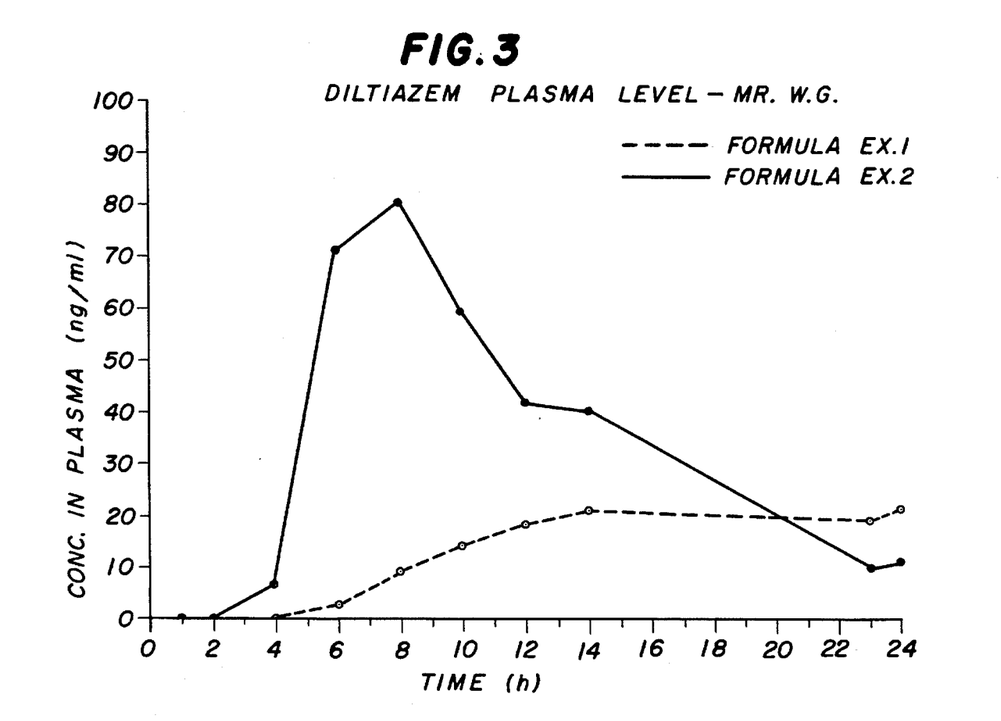
Figure 4:
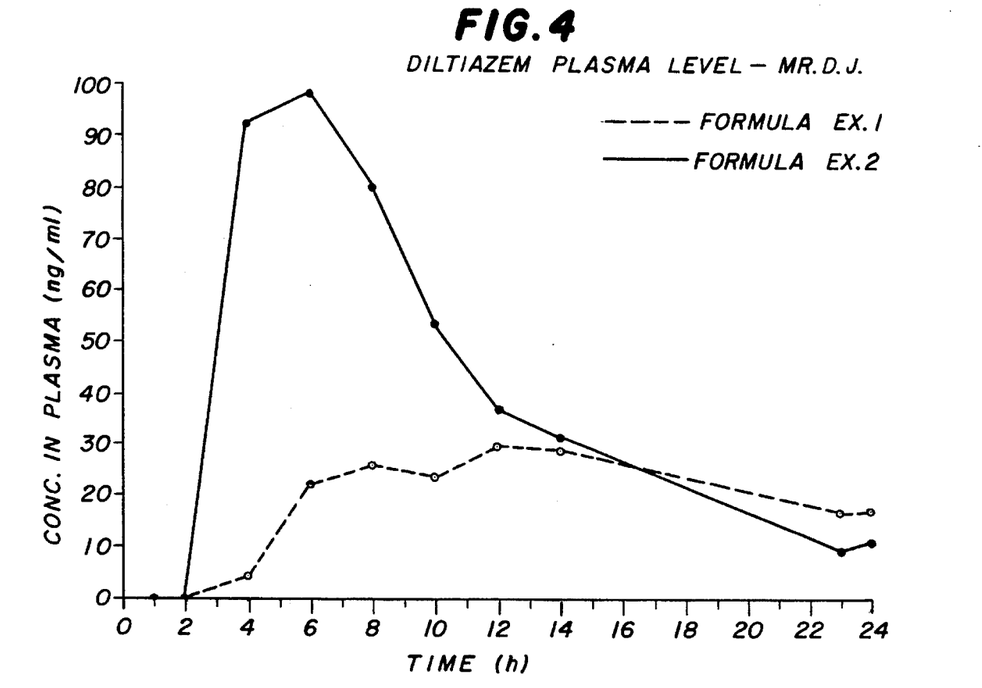
Figure 5:
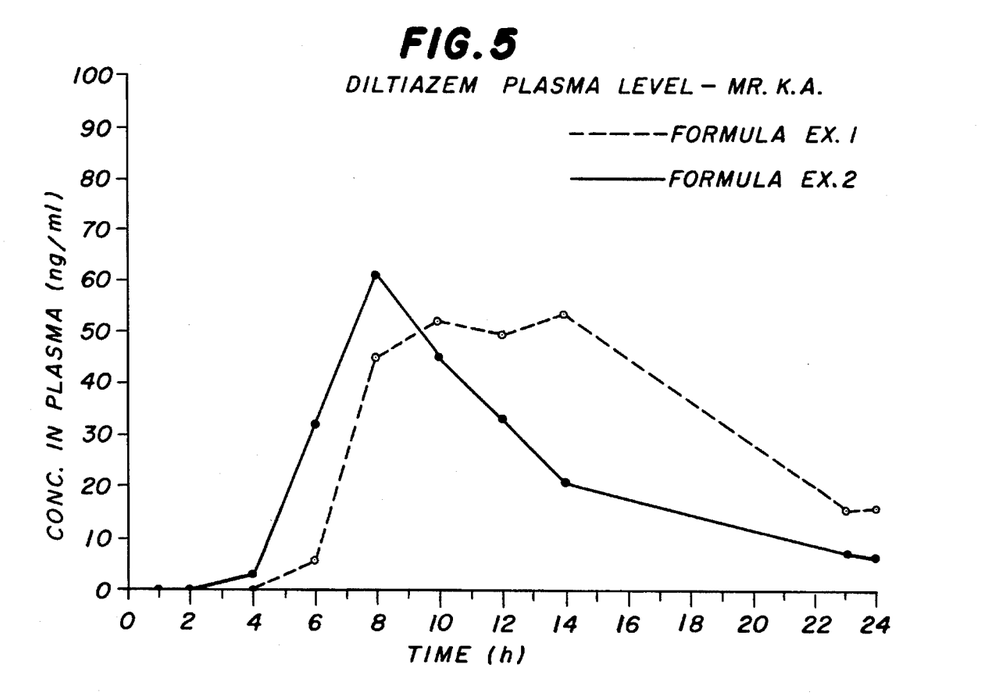
Figure 6:
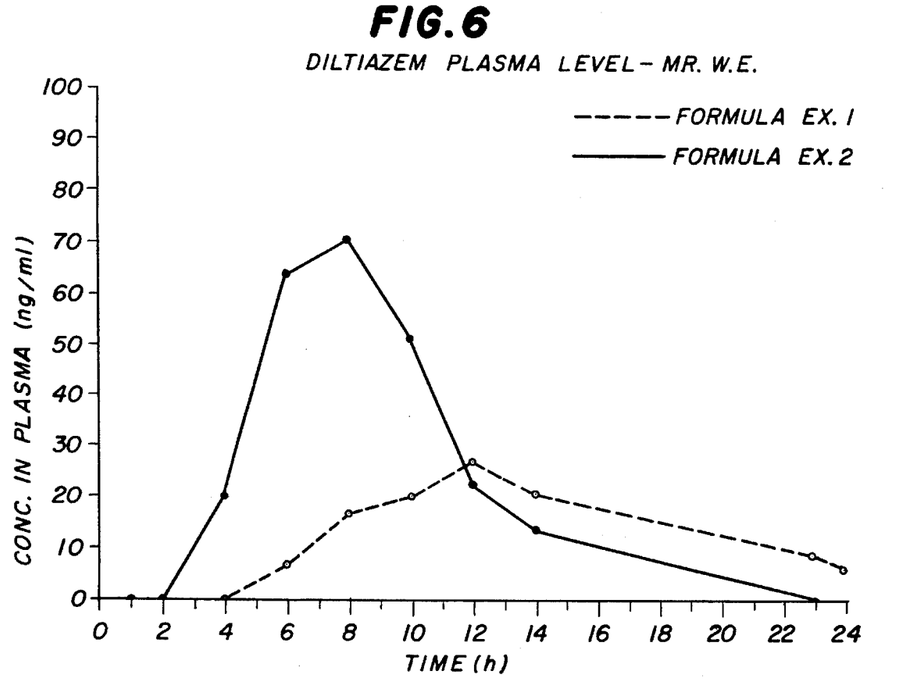
Figure 7:
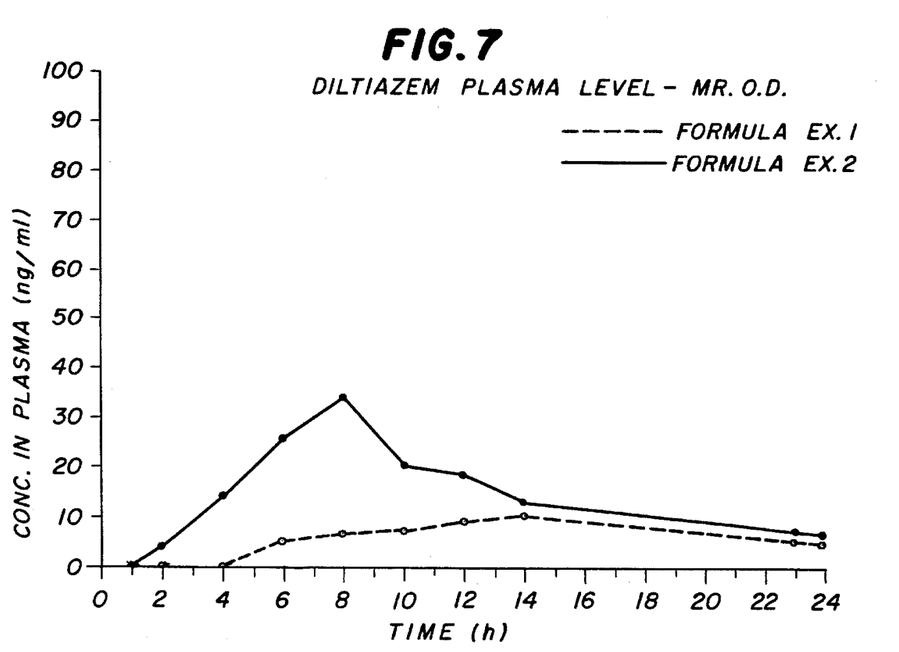

The structure of the medicinal preparation depends on the release requirements after reaching the target locations. Thus, on a nucleus containing the active substance (shown in FIG. 1 as I/II) a pH independent or pH dependent dissolving first membrane (active substance release control) (III) can be applied. The physiologically safe acid (IV) is applied onto this membrane, and on top of the acid is applied the release time-controlling compound membrane (V). The nucleus may contain one or several active substances in combination with one or several absorption enhancers, for example, 5-methoxysalicylic acid, salicylic acid and/or wetting agents, e.g., polysorbate, block copolymers of ethylene oxide and propylene oxide, ethoxylized glcyerides and/or solubilizers. Onto the compound membrane (V) another active substance layer can be applied again, if needed, and also an additional acid layer and another compound membrane layer can be added.

The amount and the nature of the applied acid in combination with the permeability of the compound membrane determine the duration of the lag phase, that is, the phase without active substance release. The permeability of the compound membrane can be adjusted, within wide limits, depending on its composition, e.g., by the use of pH-sensitive polymers, which are soluble depending on the varying pH values, mixtures of these polymers among one another, and/or pH independent dissolving or insoluble polymers, incorporation of pore-forming substances, furthermore by varying the total layer thickness, varying the pH sensitive layer thickness ratios and the insoluble components of the compound membrane, to the respective requirements for the lag phase and the nature of the active substances.

In principle, the lag phase with a pre-given composition and thickness of the compound membrane is determined by the amount of acid which prevents the dissolution of the pH sensitive polymer inner layer of the compound membrane. After the acid layer has been exhausted, the compound membrane collapses and the active substance lying underneath is released in accordance with the characteristics of the first membrane which is directly on top of it. If the active substance release-controlling first membrane is missing, the active substance is released at a maximum rate.

Example 1 describes an embodiment which releases its active substance spontaneously approximately four hours after leaving the stomach. The in vivo examination of samples, made according to examples 1 and 2, administered to six human volunteers clearly shows that the entire drug dose was reproducibly absorbed in the colon as shown in FIGS. 2 to 7. One drawing figure pertains to the test results obtained for each human volunteer. The initials for the volunteer's name is located adjacent the figure title. Diltiazem pellets of Example 2 were applied in a cross-over test. The pellets differed from those of Example 1 by elimination of the first membrane controlling the release (III, with reference to FIG. 1) and a reduced amount of acid (IV). The comparison clearly shows that the decreased amount of acid shortens the lag phase. The rapid increase of the plasma level is the result of the missing membrane (III). Since for the pellets used in this case, a stomach passage time of one to two hours is to be assumed (S. S. Davis, Top. Pharm. Sci., Proc. Int. Congr. Pharm. Sci. FIP, 43rd 1983 p. 205–215, D. D. Breimer and P. Speiser (Ed), Elsevier, Amsterdam; S. S. Davis et al. Int. J. Pharmaceutics, 21, 331–340 (1984), a lag phase in vivo totaling about five to six hours results for the formulation of Example 1, and about three to four hours for the formulation of Example 2.

This first formulation is suitable for making possible:

in combination with a partial dose, which is released over a six hour period after intake, a once-daily dose of an active substance such as, e.g., Nifedipin, Diltiazem, Verapamil etc.;

to transport targetedly and reproducibly, into the colon and to release there medical substances, which are unstable in the stomach or in the small intestine, as, for example, peptide hormones, e.g., GH-RH, LG-RH, insulin, calcitonin, and growth hormones among others. In particular, peptide pharmaceuticals can be combined for increased systemic availability in combination with absorption promoters like 5-methoxysalicylic acid, salicylic acid and others;

to administer the night before, medicinal substances, which are to be available in the early morning hours, prior to getting up, in an active plasma concentration, as, for example, an antiasthmatic, an anti-rheumatic, antiphlogistic, and nitrates. Release of the active substance is suspended during the nighttime hours, in which no therapeutic plasma concentration is necessary, in order to then increase in the early morning hours and to protect the patient against attack, e.g., asthma attack or angina pectoris attack, during or shortly prior to the wake-up phase;

to target and deliver medicaments which are to be locally active in the colon area, e.g., antibiotics, antiphlogistics, spasmolytics, and others.

The formulation in Example 2 is suited, in combination with an immediate release partial dose, to create fluctuating plasma levels. The results in vivo show that release of the active substance takes place in the small intestine and that absorption is not slowed down. This combination would correspond to two applications of a single dose quick-release type at an interval of four hours. This is a requirement, for example, which is made for therapy with organic nitrates. By this invention the creation of a tolerance can be avoided.

The Example 3 shows that with the active substance isosorbid dinitrate the lag phase, within the expected physiological pH value, is independent of the surrounding environment (compare the active substance release of examples 1 and 2). The conditions of the milieu are chosen so that dissolution of the pH sensitive portion of the compound membrane would have to occur without a compound membrane according to this invention.

Example 4 shows the influence of the composition on the release in vitro by means of isosorbid dinitrate pellets, where, in comparison to Example 3, the acid amount is halved, but the pH sensitive portion of the compound membrane is doubled. This proves that, within the compound membrane, not the thickness of the pH sensitive layer, but the amount of employed acid together with the compound membrane, are necessary for time control. For comparison in Example 5, the active substance release time of pellets is shown in only the pH sensitive portion of the compound membrane present. A lag phase and consequently a time controlled active substance release is not detectable.

Example 1

| Composition | |
|---|---|
| 1 diltiazem-HCl | 50.0g |
| 2 sugar pellets | 50.0g |
| 3 hydroxypropyl cellulose | 1.0g |
| 4 cellulose acetate phthalate | 7.5g |
| 5 succinic acid | 25.0g |
| 6 ethyl cellulose | 6.0g |
| 7 hydroxypropyl cellulose | 6.0g |
| 8 cellulose acetate phthalate | 7.5g |
| 9 ethyl cellulose | 1.0g |

Manufacture

The active substance (1) is applied onto the sugar pellets (2) in a suitable container by means of an adhesive solution which consists of the adhesive (3) dissolved in a suitable solvent. Onto the active substance layer is applied: a first membrane of cellulose acetate phthalate (4) and onto this, a layer of acid (5) in a fluidized bed vessel with the aid of an adhesive solution-dispersion of 6 and 7 in a suitable solvent or dispersion means. Onto the acid layer again, also in the fluidized bed vessel, the compound membrane of cellulose acetate phthalate (8) (the pH sensitive polymer inner layer) and ethyl cellulose (9) (the insoluble polymer outer layer) are applied in a suitable solvent or dispersion means.

Active Substance Release

Method: Rotating bottle NF XIII, modified pH change after four hours from ph 5.5 to ph 7.5

| | Released Active Substance | |
|---|---|---|
| Time (h) | pH 5.5 | pH 7.5 |
| 2 | 0.2% | |
| 4 | 0.7% | |
| 6 | | 7.0% |
| 8 | | 22.0% |
| 10 | | 39.0% |

Example 2

The manufacture of the diltiazem pellets takes place as in Example 1. However, the first membrane controlling the release and made of cellulose acetate phthalate and located directly on top of the active substance layer is omitted. The succinic acid is reduced to 20%.

| Composition | |
|---|---|
| 1 diltiazem-HCl | 50.0g |
| 2 sugar pellets | 50.0g |
| 3 hydroxypropyl cellulose | 1.0g |
| 4 succinic acid | 5.0g |
| 5 ethyl cellulose | 6.0g |
| 6 hydroxypropyl cellulose | 6.0g |
| 7 cellulose acetate phthalate | 7.5g |
| 8 ethyl cellulose | 1.0g |

Item 3 is an adhesive; item 4 is the safe acid; items 5 and 6 are adhesives used to apply the safe acid layer; item 7 forms the pH sensitive polymer inner layer of the compound membrane; and item 8 forms the insoluble polymer outer layer of the compound membrane.

Active Substance Release Method: Rotating bottle NF XIII pH change after four hours from pH 5.5 to pH 7.5

| | Released Active Substance | |
|---|---|---|
| Time (h) | pH 5.5 | pH 7.5 |
| 2 | 0.4% | |
| 4 | 14.7% | |
| 6 | | 63.0% |
| 8 | | 102.0% |

Example 3

| Composition | |
|---|---|
| 1 isosorbid dinitrate/lactose 40/60 | 83.3 g |
| 2 sugar pellets | 50.0 g |
| 3 hydroxypropyl cellulose | 3.3 g |
| 4 succinic acid | 70.0 g |
| 5 ethyl cellulose | 8.4 g |
| 6 hydroxypropyl cellulose | 8.4 g |
| 7 eudragit L | 15.4 g |
| 8 triacetin | 2.4 g |
| 9 talcum | 2.7 g |
| 10 ethyl cellulose | 2.5 g |
| 11 macrogol 1500 | 0.25g |
| 12 talcum | 0.25g |

The listed items are as defined in Example 3 except as follows: Eudragit L is an anionic copolymer derived from methacrylic acid and methyl methacrylate having about a 1:1 ratio of free carboxy groups to ester groups and a mean molecular weight of about 135,000. It forms the pH sensitive polymer inner layer of the compound membrane. Item 10 forms the insoluble polymer outer layer of the compound membrane. Item 8 is glyceryl triacetate and is a softener for the eudragit L layer. Macrogol 1500 (item 11) is the international name for polymerized polyethylene glycol and it functions as a film softener for ethyl cellulose.

Manufacture

Onto the sugar pellets (2), a mixture of isosorbid dinitrate and lactose (1) is applied in a container by means of an adhesive solution consisting of the adhesive (3) and a suitable solvent. Thereon the acid (4) is applied in a fluidized bed vessel by means of a solution of adhesives (5) and (6). Also applied onto the acid layer in the fluidized bed vessel is the compound membrane consisting of eudragit L with the auxiliary substances triacetin and talcum (items 7 to 9) and an outer insoluble layer of ethyl cellulose with the auxiliary substances macrogol 1500 and talcum (items 10 to 12).

Active Substance Release 1

Method: Rotating bottle NF XIII, mod. pH change after four hours from pH 5.5 to pH 6.0

|          | Released Active Substance | |
| -------- | ------ | ------ |
| Time (h) | pH 5.5 | pH 6.0 |
| 2 | 3.5% | |
| 4 | 8.2% | |
| 6 | | 39.2% |

Active Substance Release 2

Method: Rotating Bottle NF XIII, mod.

| Time (h) | Released Active Substance pH value = 6.0 |
| --- | --- |
| 1 | 1.3% |
| 2 | 2.9% |
| 3 | 4.5% |
| 4 | 9.3% |
| 5 | 24.8% |
| 6 | 44.2% |

Example 4

| Composition | |
| --- | --- |
| 1 isosorbid dinitrate/lactose 40/60 | 83.3 g |
| 2 sugar pellets | 50.0 g |
| 3 hydroxypropyl cellulose | 3.3 g |
| 4 succinic acid | 35.0 g |
| 5 ethyl cellulose | 8.4 g |
| 6 hydroxypropyl cellulose | 8.4 g |
| 7 eudragit L | 30.8 g |
| 8 triacetin | 2.25g |
| 9 talcum | 2.25g |
| 10 ethyl cellulose | 2.5 g |

-continued

| Composition | |
| --- | --- |
| 11 macrogol 1500 | 0.25g |
| 12 talcum | 0.5 g |

The manufacture takes place analogously. The succinic acid amount is halved, the eudragit amount is doubled.

Onto the sugar pellets (item 2), a mixture of isorbid dinitrate and lactose (item 1) is applied in a container by means of an adhesive solution consisting of the adhesive (item 3) and a suitable solvent. Thereon, the succinic acid (item 4) is applied in a fluidized bed vessel by means of a solution of adhesives (items 5 and 6). Also applied onto the acid layer in the fluidized bed vessel is the compound membrane consisting of an inner layer of eudragit L with the auxiliary substances triacetin and talcum (items 7 to 9) and ethyl cellulose with the auxiliary substances macrogol 1500 and talcum (items 10 to 12).

Active Substance Release

Method: Rotating Bottle NF XIII pH change after four hours from pH 6.0 to pH 7.5

|          | Released Active Substance | |
| -------- | ------ | ------ |
| Time (h) | pH 6.0 | pH 7.5 |
| 2 | 17.9% | |
| 4 | 70.9% | |
| 6 | | 95.3% |

Example 5

The manufacture of the isosorbid dinitrate pellets takes place as in Example 4. The ethyl cellulose insoluble polymer layer portion (item 10) of the compound membrane however is left out.

Active Substance Release 1

Method: Rotating Bottle NF XIII pH change after four hours from pH 6.0 to pH 7.5

|          | Released Active Substance | |
| -------- | ------ | ------ |
| Time (h) | pH 6.0 | pH 7.5 |
| 2 | 54.2% | |
| 4 | 92.8% | |
| 6 | | 102.9% |

Active Substance Release 2

Method: Rotating Bottle NF XIII, mod. pH change after four hours from pH 5.5 to pH 7.5

|          | pH Value | |
| -------- | --- | --- |
| Time (h) | 5.5 | 7.5 |
| 2 | 2.0% | |

-continued

| Time (h) | pH Value | |
| --- | --- | --- |
| | 5.5 | 7.5 |
| 4 | 4.5% | |
| 6 | | 68.9% |

We claim:

1. Pharmaceutical preparation to be administered orally, comprising:

a physiologically safe solid nucleus;

the nucleus being enveloped by an active substance layer containing at least one pharmacologically active substance;

an acid layer comprising at least one physiologically safe solid acid over the layer containing the pharmacologically active substance; and a compound membrane over the acid layer, the compound membrane consisting of two discrete layers including a pH sensitive polymer inner layer adjacent the acid layer and an insoluble polymer outer layer adjacent the pH sensitive polymer inner layer, said outer layer being permeable to gastrointestinal secretions.

2. Pharmaceutical preparation according to claim 1 comprising:

a first membrane layer consisting of cellulose acetate phthalate between the active substance layer and the acid layer.

3. Pharmaceutical preparation to be administered orally, comprising:

a physiologically safe solid nucleus including at least one pharmacologically active substance;

an acid layer comprising at least one physiologically safe solid acid over the nucleus; and a compound membrane over the acid layer, the compound membrane consisting of two discrete layers including a pH sensitive polymer inner layer adjacent the acid layer and an insoluble polymer outer layer adjacent the pH sensitive polymer inner layer, said outer layer being permeable to gastrointestinal secretions.

4. A pharmaceutical preparation according to claim 3 comprising:

a fist membrane layer consisting of cellulose acetate phthalate between the nucleus and the acid layer.

5. Pharmaceutical preparation to be administered orally, comprising:

a physiologically safe solid nucleus;

the nucleus being enveloped by a layer containing at least one pharmacologically active substance and at least one physiologically safe solid acid; and a compound membrane over the layer containing the active substance and the physiologically safe acid, the compound membrane consisting of two discrete layers including a pH sensitive polymer inner layer adjacent the acid layer and an insoluble polymer outer layer adjacent the pH sensitive polymer inner layer, said outer layer being permeable to gastrointestinal secretions.

6. Pharmaceutical preparation according to claims 1, 2, 3, 4 or 5 in which the compound membrane pH sensitive polymer inner layer comprises a polymer selected from the group consisting of copolymers of methacrylic acid and methacrylic acid methylester, carboxymethylethyl cellulose, cellulose acetate phthalate, cellulose acetylphthalate, cellulose diacetylphthalate, cellulose triacetylphthalate, hydroxypropylmethyl cellulose phthalate, sodium cellulose acetatephthalate, cellulose esterphthalate, cellulose etherphthalate, cellulose esterphthalate, cellulose etherphthalate, cellulose esteretherphthalate, hydroxypropyl cellulose phthalate, methyl cellulose phthalate, keratin, and mixtures thereof.

7. Pharmaceutical preparation according to claims 1, 2, 3, 4 or 5 in which the compound membrane insoluble polymer outer layer comprises a polymer selected from the group consisting of cellulose ether, a copolymerisate of acrylic and methacrylic acid esters with quaternary ammonium groups, polyvinylacetate and mixtures thereof.

8. Pharmaceutical preparation according to claim 1 in which the polymer portion of the insoluble polymer layer of the compound membrane amounts to 1 to 30 percent per weight of the compound membrane.

9. Pharmaceutical preparation according to claims 1, 2, 3, 4 or 5 in which the acid layer comprises sodium dihydrogenphosphate, citric acid, tartaric acid, succinic acid, fumaric acid and mixtures thereof.

10. A method of producing a pharmaceutical preparation for oral administration comprising:

applying a layer containing a pharmacologically active substance onto a physiologically safe nucleus;

applying a layer of a physiologically safe acid onto the layer of active substance;

applying a pH sensitive polymer layer to the acid layer; and applying an insoluble polymer layer to the pH sensitive polymer layer.

11. A method according to claim 10 in which:

a first membrane layer consisting of cellulose acetate phthalate is applied between the active substance layer and the acid layer.

12. A method of producing a pharmaceutical preparation for oral administration comprising:

preparing a physiologically safe solid nucleus including at least one pharmacologically active substance;

applying a layer of a physiologically safe solid acid over the nucleus;

applying a pH sensitive polymer layer to the acid layer; and applying an insoluble polymer layer to the pH sensitive polymer layer, said insoluble polymer layer being permeable to gastrointestinal secretions.

13. A method according to claim 12, in which:

a first membrane layer consisting of cellulose acetate phthalate is applied between the nucleus and the acid layer.

14. A method of producing a pharmaceutical preparation for oral administration comprising:

applying to a physiologically safe solid nucleus a layer containing at least one pharmacologically active substance and at least one physiologically safe solid acid;

applying a pH sensitive polymer layer to the layer containing the active substance and the safe acid; and applying an insoluble polymer layer to the pH sensitive polymer layer, said insoluble polymer layer being permeable to gastrointestinal secretions.

15. A method according to claims 10, 11, 12, 13 or 14 in which the pH sensitive polymer is selected from the group consisting of copolymers of methacrylic acid and methacrylic acid methylester, carboxymethylethyl cellulose, cellulose acetate phthalate, cellulose acetylphthalate, cellulose diacetylphthalate, cellulose triacetylphthalate, hydroxypropylmethyl cellulose phthalate, sodium cellulose acetatephthalate, cellulose esterphthalate, cellulose etherphthalate, cellulose esteretherphthalate, hydroxypropyl cellulose phthalate, methyl cellulose phthalate, keratin, and mixtures thereof.

16. A method according to claims 10, 11, 12, 13 or 14 in which the acid layer comprises sodium dihydrogenphosphate, citric acid, tartaric acid, succinic acid, fumaric acid and mixtures thereof.

17. A method according to claims 10, 11, 12, 13 or 14 in which the insoluble polymer is selected from the group consisting of cellulose ether, a copolymerisate of acrylic and methacrylic acid esters with quaternary ammonium groups, polyvinylacetate and mixtures thereof.

18. A pharmaceutical preparation according to claim 1 in which:

the acid layer protects the pH sensitive polymer inner layer of the compound membrane against dissolution in gastrointestinal fluids until the acid layer is exhausted; and the insoluble polymer outer layer of the compound member does not dissolve in the gastrointestinal fluids and permits the active substance to permeate it after dissolution of the pH sensitive polymer inner layer of the compound membrane by gastrointestinal fluids.

19. A pharmaceutical preparation according to claim 2 in which:

the acid layer protects the first membrane layer between the active substance layer and the acid layer, and also protects the pH sensitive polymer inner layer of the compound membrane, against dissolution in gastrointestinal fluids until the acid layer is exhausted; and the insoluble polymer outer layer of the compound member does not dissolve in gastrointestinal fluids and permits the active substance to permeate it after dissolution of the first membrane layer and the pH sensitive polymer inner layer by gastrointestinal fluids.

* * * * *

UNITED STATES PATENT AND TRADEMARK OFFICE
CERTIFICATE OF CORRECTION

PATENT NO. : 5,472,710

DATED : December 5, 1995

INVENTORS : KLOKKERS-BETHKE ET AL.

It is certified that error appears in the above-identified patent and that said Letters Patent is hereby corrected as shown below:

Column 4, line 63, "As is" should be --As it--.

Column 7, line 5, "88614 892" should be --886-892--.

Column 7, line 14, "dissolution, of" should be --dissolution of--.

Column 7, line 52, "glcyerides" should be --glycerides--.

Column 9, line 27, "shown in" should be --shown with--.

Column 9, line 67, "ph 5.5 to ph 7.5" should be --pH 5.5 to pH 7.5--.

Column 10, lines 37-38, "Active Substance Release Method: Rotating bottle NF XIII pH change" should be
       --Active Substance Release Method
Rotating bottle NF XIIX
   pH change--.

Column 12, line 11, "of isorbid" should be --of isosorbid--.

Column 13, line 13, "a physiologically safe solid nucleus" should be --a sugar nucleus--.

Column 13, line 33, "a physiologically safe solid nucleus" should be --a sugar nucleus--.

UNITED STATES PATENT AND TRADEMARK OFFICE
CERTIFICATE OF CORRECTION

PATENT NO. : 5,472,710
DATED : December 5, 1995
INVENTORS : KLOKKERS-BETHKE ET AL.

It is certified that error appears in the above-identified patent and that said Letters Patent is hereby corrected as shown below:

Column 13, line 51, "a physiologically safe solid nucleus" should be --a sugar nucleus--.

Column 13, line 46, "a fist" should be --a first--.

Column 14, line 40, "a physiologically safe solid nucleus" should be --a sugar nucleus--.

Column 14, line 56, "a physiologically safe solid nucleus" should be --a sugar nucleus--.

Column 15, lines 9-10, "dihydrogenphosphate" should be --dihydrogen phosphate--.

Signed and Sealed this

Thirtieth Day of July, 1996

Attest:

BRUCE LEHMAN

*Attesting Officer*  *Commissioner of Patents and Trademarks*